United States Patent [19]

Howe

[11] Patent Number: 5,242,405
[45] Date of Patent: Sep. 7, 1993

[54] SYRINGE HAVING GRAPHICS VISUALIZATION FEATURES

[75] Inventor: Wesley J. Howe, Franklin Lakes, N.J.

[73] Assignee: Becton, Dickinson and Company, Franklin Lakes, N.J.

[21] Appl. No.: 893,182

[22] Filed: Jun. 3, 1992

Related U.S. Application Data

[63] Continuation-in-part of Ser. No. 308,231, Feb. 8, 1989, abandoned.

[51] Int. Cl.⁵ .............................................. A61M 1/00
[52] U.S. Cl. .................................. 604/125; 604/189; 604/218; 73/864.16
[58] Field of Search ............... 73/327, 864.16; 604/51, 604/125, 184, 187, 189, 218, 207; 222/158

[56] References Cited

U.S. PATENT DOCUMENTS

| | | |
|---|---|---|
| 2,586,581 | 2/1952 | Tschischeck . |
| 2,888,015 | 5/1959 | Hunt ............................. 73/864.16 |
| 4,724,508 | 2/1988 | Macy . |
| 4,743,121 | 5/1988 | Takagi et al. . |
| 5,062,828 | 11/1991 | Waltz ................................. 604/51 |

Primary Examiner—C. Fred Rosenbaum
Assistant Examiner—Michael Rafa
Attorney, Agent, or Firm—John L. Voellmicke

[57] ABSTRACT

A syringe barrel having graphics visualization features includes an elongate body portion having a longitudinal axis and a side wall spaced from the axis defining an inside diameter and a chamber for retaining fluid. The side wall includes a transparent portion having indicia and contrast means of substantially uniform color opposed from the indicia for improving readability of the indicia.

21 Claims, 4 Drawing Sheets

SYRINGE HAVING GRAPHICS VISUALIZATION FEATURES

This is a continuation in part of application Ser. No. 308,231 filed Feb. 8, 1989, now abandoned.

BACKGROUND OF THE INVENTION

1. Field of the Invention

The present invention relates to syringes and more particularly concerns syringe barrels having features to improve graphics visualization.

2. Description of Related Information

Generally speaking, a hypodermic syringe consists of a cylindrical barrel, most commonly made of thermoplastic material or glass, having a distal end connected to a sharpened needle cannula or adapted to be connected to a hypodermic needle assembly and a proximal open end adapted to receive a stopper and plunger rod assembly. One of the purposes of the stopper is to provide a relatively fluid tight seal between itself and the syringe barrel so that movement of the stopper along the barrel will cause liquid to be drawn into or forced out of the syringe through the distal end. The stopper is moved along the syringe barrel by applying axial force to a rigid plunger rod which is connected to the stopper and is sufficiently long to be accessible outside of the barrel.

Syringes usually contain indicia such as volume measuring indicia on the side of the barrel to indicate the volume of liquid contained within the syringe. It is desirable for convenient use and to prevent medical error to provide volume measuring indicia which are clear and easy to read by the person filling the syringe and/or administrating medication using the syringe. The need for easy to read graphics on a syringe barrel is especially acute with respect to diabetics who, after many years of affliction, suffer various side effects of this disease and its treatment such as failing vision. Diabetics also are believed to suffer from temporary periods of blurred vision. To this end the art teaches devices for attachment to syringes for the purpose of magnifying the volume measuring indicia. Such a device is taught in U.S. Pat. No. 2,586,581 to Tschischeck. Tschischeck teaches a magnifying attachment for syringes and similar instruments which contains a pair of parallel spaced elongated wire loops which are embedded in the bottom wall of an elongated section which performs the magnification function. The loops are designed to engage the syringe by snap on movement. The magnifying attachment stays with the syringe until it is removed for various reasons such as for use on another syringe.

Additional teachings in the prior art address improving the readability of volume measuring indicia by providing higher quality volume measuring indicia on the syringe barrel. In particular, a corona discharge treatment of the surface of various formed plastic articles such as syringe barrels will improve the compatibility of the surface with printing inks to provide higher quality printed indicia. Such a method is taught by Macy in U.S. Pat. No. 4,724,508.

Many hypodermic syringe barrels are made of glass or transparent plastic having graphics such as volume measuring indicia along their side walls. Improved quality of volume measuring indicia will not be enough if the transparent syringe barrel is held near a background which is similar in color and/or shade to the graphics. Under these conditions the graphics may be difficult to observe. Also, separate attachable magnifying devices will not overcome problems in this area.

Although the art has provided teachings directed toward improving the readability of indicia such as volume measuring indicia on a syringe barrel wall through the use of separate devices and improved printing there is still a need for a simple, straight forward, reliable, easily fabricated syringe barrel having means to improve the readability of the volume measuring indicia without the use of separate additional elements, devices or holders. There is also need to improve readability of the volume measuring indicia when the syringe is used in the background which is a similar color or shade to the volume measuring indicia.

SUMMARY OF THE INVENTION

An operable syringe barrel having graphics visualization features of the present invention includes an elongate body portion having a longitudinal axis and a side wall spaced from the axis defining an inside diameter and a chamber for retaining fluid. The side wall includes a transparent portion having indicia. The side wall also includes contrast means opposed from the indicia for improving the readability of the indicia. The contrast means is of substantially uniform color and has a chordal width of about equal or greater than the inside diameter of the elongate body portion.

In accordance with another embodiment of the present invention, a syringe barrel having graphics visualization features includes an elongate body portion having a longitudinal axis and a circularly shaped side wall spaced from said axis defining an inside diameter and a chamber for retaining fluid. The body portion includes an open proximal end and a distal end having a passageway therethrough in fluid communication with the chamber. The side wall includes a transparent portion having volume measuring indicia running axially along the side wall. The side wall also includes contrast means opposed from the volume measuring indicia for improving readability of the volume measuring means. The contrast means includes a substantially axially oriented elongate substantially uniform opaque coating on the side wall. The contrast means has a chordal width of about equal or greater than the inside diameter of the elongate body portion.

DETAILED DESCRIPTION

Figure 1:
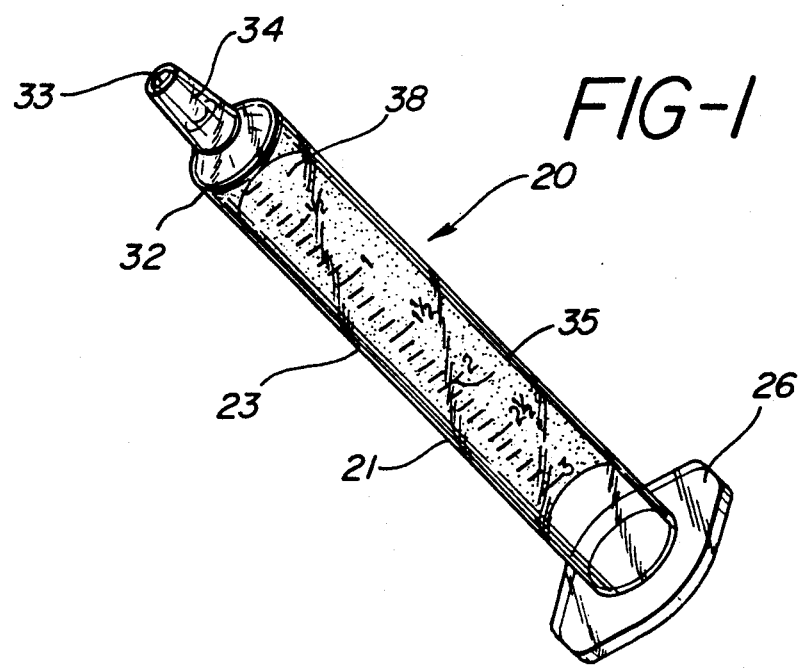
FIG. 1 is a perspective view of the syringe barrel of the present invention.
Figure 4:
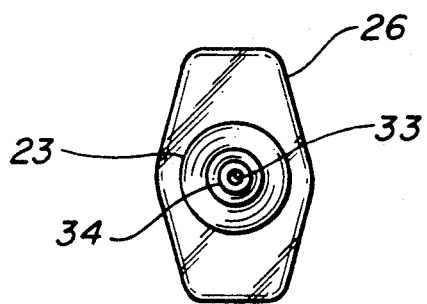
FIG. 4 is a side elevation view of the distal end of the syringe barrel of FIG. 3.
Figure 5:
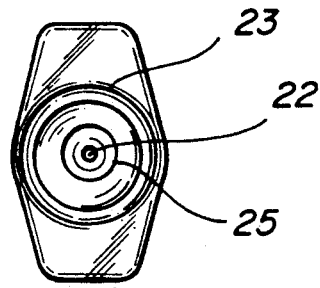
FIG. 5 is a side elevation view of the proximal end of the syringe barrel of FIG. 3.
Figure 2:
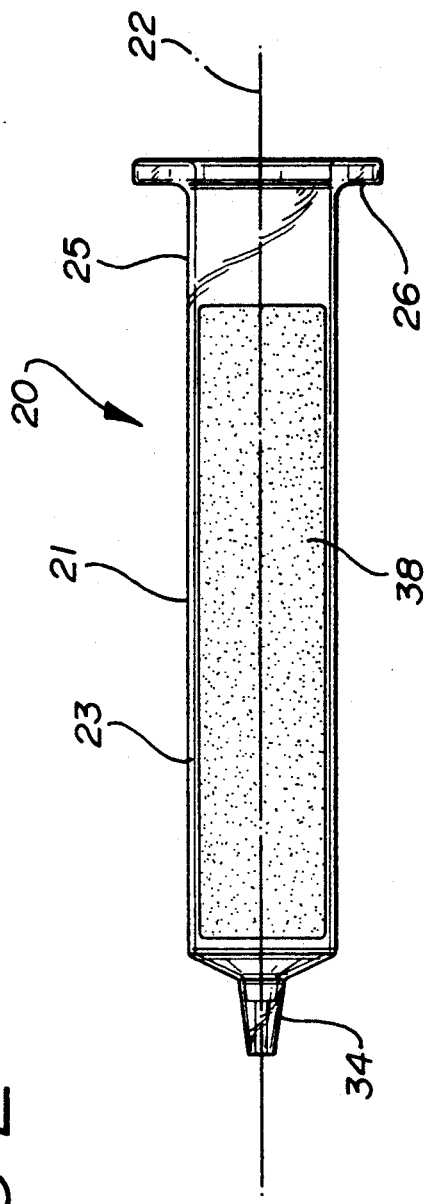
FIG. 2 is a side elevation view of the syringe barrel of FIG. 1 viewed from the rear of the syringe barrel.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-7, a syringe barrel 20, having graphics visualization features, includes an elongate body portion 21 having a longitudinal axis 22. A circularly shaped side wall 23, spaced from axis 22, defines an inside diameter D and a chamber 25 for retaining fluid. Body portion 21 includes an open proximal end 31 and a distal end 32 having a passageway 33 therethrough in fluid communication with the chamber. A tapered frusto-conically shaped tip 34 extends outwardly from the distal end of said body portion. This tip is adapted to accept known hypodermic needle assemblies and/or other fluid delivery means such as stopcocks and adapters. A flange 26 is also provided at the proximal end of the body portion to facilitate handling and positioning the syringe barrel.

For the purposes of the description of the present invention, the term "distal end" is meant to refer to the end furthest from the person holding the syringe, whereas the term "proximal end" is meant to refer to the end closest to the holder of the syringe.

Side wall 23 includes volume measuring indicia 35 for use in determining the volume of medication in the syringe barrel and, accordingly, the volume of medication to be dispensed. That portion of the side wall containing the volume measuring indicia should be substantially transparent so that the user may see the liquid contents within the chamber in order to measure the volume. In this embodiment transparent portion 37 of the barrel not only includes the portion of the side wall containing the volume measuring indicia but the entire barrel is molded of transparent material.

In the 1960's the polymers that were most suitable for molding hypodermic syringe barrels produced a somewhat foggy or translucent syringe barrel. Moldable polymers that could produce a more transparent glass-like barrel tended to be brittle and had deficiencies that did not justify their use in syringe barrels. Modern polymer technology is producing moldable thermoplastic resins which are more desirable for hypodermic syringes in that they lack brittleness and are resistant to sterilization procedures while having improved clarity. However, with a more transparent barrel, the graphics or indicia, which usually include volume measuring indicia printed on the barrel in a dark color or in black, can be more difficult to read. This is especially true if the syringe barrel is positioned near a dark background which does not contrast well with the volume measuring indicia. It is sometimes difficult to easily visualize volume measuring indicia on any syringe barrel and especially on barrels made of more transparent materials. To this end the instant invention provides contrast means opposed from the volume measuring indicia for improving the readability of the volume measuring indicia. In this embodiment contrast means includes a contrast coating 38 on the side wall. The coating in this embodiment is substantially axially oriented and elongately shaped to cover approximately the same length of the side wall as the volume measuring indicia.

Figure 3:
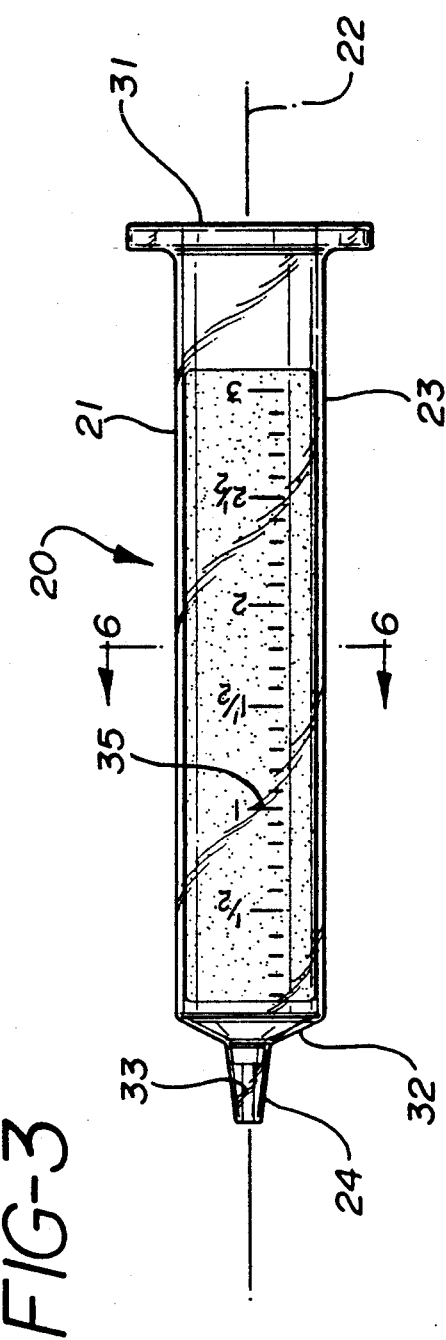
FIG. 3 is a side elevation view of the syringe barrel of FIG. 1 viewed from the front of the syringe barrel.
Figure 6:
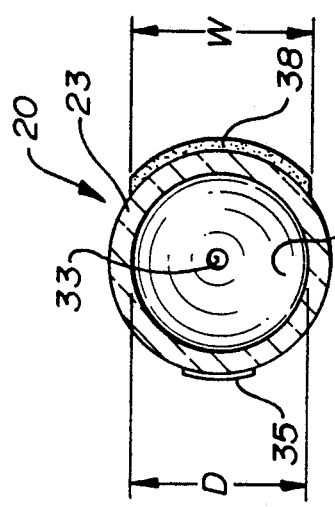
FIG. 6 is a cross-sectional view of the syringe of FIG. 3 taken along line 6—6 with the thickness of the contrast coating and the volume measuring indicia exaggerated.
Figure 7:
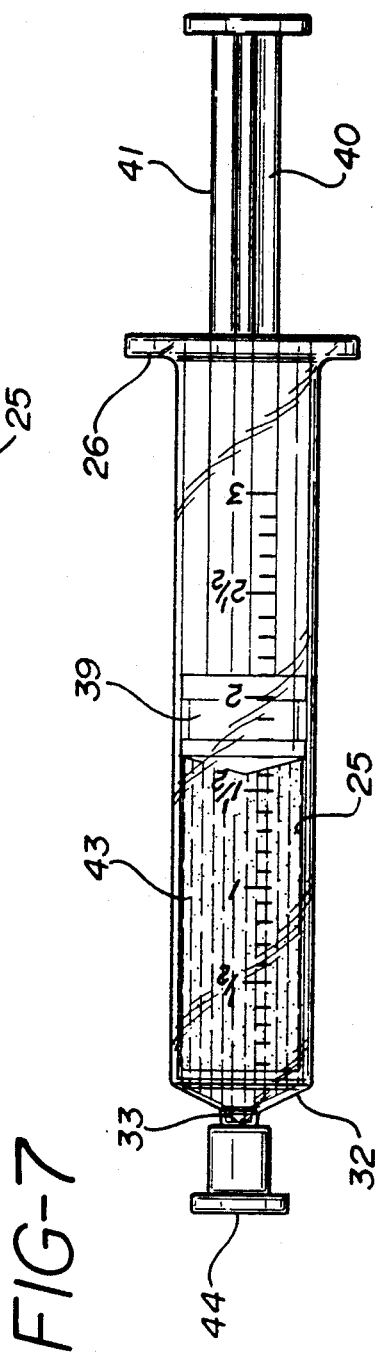
FIG. 7 is a side elevation view of the syringe barrel of FIG. 1 further including a plunger rod, stopper, liquid mediation and a tip cap.

The coating is positioned approximately across from or on the opposite side of the barrel so that a person viewing the volume measuring indicia from a line of sight which is perpendicular to the side wall, as best illustrated in FIG. 3, will also see the contrast coating on the other side of the barrel. It is within the purview of the instant invention to include contrast means opposed from the volume measuring indicia so that an observer viewing the syringe barrel from the side of the volume measuring indicia can orient the syringe so that at least a portion of the volume measuring indicia and a portion of the contrast means can be seen along the same line of sight with a portion of the chamber being between the indicia and the contrast means. However, it is preferred that the contrast coating be distributed over a wide portion of the syringe barrel so that little or no angular manipulation of the barrel is necessary to orient the syringe so that the volume measuring indicia can be seen along the same line of sight as the contrast coating. To achieve this objective, as best illustrated in FIG. 6, the contrast means of this embodiment is coated on the outside diameter of the barrel for a sufficient number of degrees so that its chordal width W is about equal or greater than the inside diameter D of the elongate body portion of the barrel. It can be seen that this broad coverage of the contrast means over the barrel will make it easier for the user to align the volume measuring indicia with the contrast means and less likely that the volume measuring indicia and the contrast means will be misaligned so that the user does not have the advantage of the improved graphics visualization features of the invention.

It is the objective of the contrast coating to make the volume measuring indicia easier to see clearly. In this embodiment it is preferable that the volume measuring indicia are black while the contrast coating is white or bright yellow.

In the preferred embodiment volume measuring indicia 35 are applied to side wall 23 using an ink printing process. It will be apparent to one skilled in the art that there are numerous ways to apply volume measuring indicia to an article such as a syringe barrel such as printing with ink or hot stamp printing ribbon or molding the volume measuring indicia in the barrel as raised projections which may be later printed or coated for improved visibility. It is within the purview of the instant invention to include all these various means for providing volume measuring indicia and the printing process described hereinabove is intended to be exemplary of these many possibilities.

Also, it will be apparent to one skilled in the art that there are numerous ways to apply or obtain contrast means on a syringe barrel side wall. Contrast means may be an applied coating or a printed area on the inside diameter or the outside diameter of the side wall or may consist of a surface treatment using abrasive machining techniques such as sandblasting or roughening or texturing with tools. Contrast means can also be molded in through mold texturing or by use of two-color molding or even an extrusion processes using two different thermoplastic materials as will be described in more detail hereinafter. Contrast means in this preferred embodiment is an applied coating made by a printing process similar to the volume measuring indicia. The term "coating" as used herein is intended to include all means for providing an applied coating including printing. The applied contrast coating is meant to be exemplary of the many possibilities of providing contrast means which renders that portion of the barrel less transparent than the portion of the barrel containing the volume measuring indicia for improving the readability of the volume measuring indicia.

Darker colors and black are preferred for the volume measuring indicia while brighter colors and lighter colors including red, yellow and blue and combinations thereof are desirable for the contrast coating with yellow on white being preferred. An opaque contrast coating is also preferred.

It is known that certain surface treatments of a plastic syringe barrel will enhance printability and adhesion of printing inks. In particular, a corona discharge treatment of the surface of various plastic articles such as syringe barrels will improve the compatibility of the surface of the article with printing inks. Such a method is taught by Macy in U.S. Pat. No. 4,724,508. Such a method is desirable for manufacturing syringe barrels of the instant invention.

It should be noted that the present invention provides contrast means for improving the readability of the volume measuring indicia without the use of separate additional elements, devices, holders or the like. After manufacturing the volume measuring indicia and contrast means are part of the syringe barrel itself and generally speaking cannot be removed without destroying the indicia and/or the contrast means.

The syringe barrel of the present invention may be used with plunger means having a stopper 39 and a plunger rod 40 to form a syringe assembly. Stopper 39 is slidably positioned in fluid tight engagement inside syringe barrel 20 and is capable of moving fluid from chamber 25 through passageway 33 upon its movement toward distal end 32. Said stopper is also capable of facilitating the drawing of fluid into chamber 25 through passageway 33 upon its movement away from distal end 32. Plunger rod 40 includes elongate body portion 41 engaging stopper 39 to facilitate operation of the stopper. Body portion 41 extends outwardly from open proximal end 31 of the syringe barrel.

The syringe assembly may be filled with liquid medication 43 facilitated by the improve graphics visualization features of the present invention. If the syringe is not used immediately to inject medication, a sealing means such as resilient tip cap 44 may be used for releasably sealing the passageway to retain medication 43 in the chamber.

Figure 8:
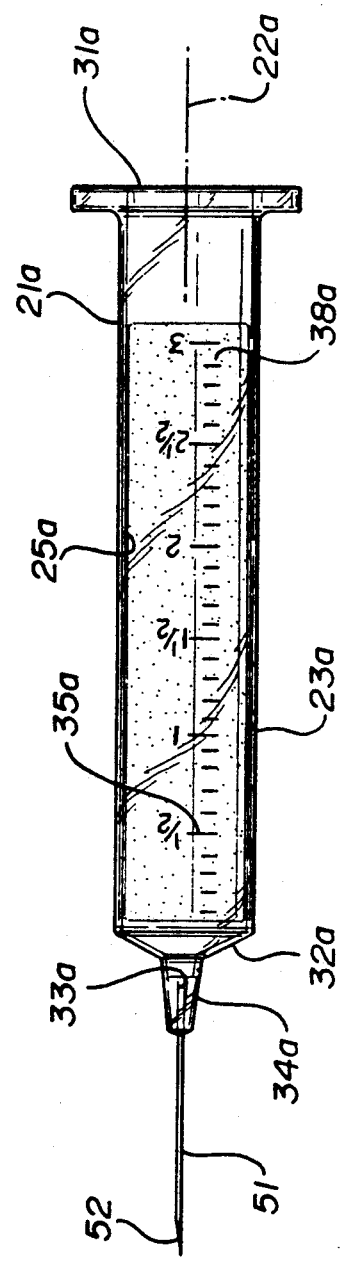
FIG. 8 is a side elevational view of an alternative embodiment of the syringe barrel of the present invention.

Referring now to FIG. 8, an alternative embodiment of the syringe barrel of the instant invention is illustrated. In this alternative embodiment the structure of the syringe barrel is substantially similar to the syringe barrel of the embodiment of FIGS. 1–7. Accordingly, substantially similar components that perform substantially similar functions will be numbered identically to those components of the embodiment of FIGS. 1–6 except a suffix "a" will be used to identify those components in FIG. 8. In this alternative embodiment a syringe barrel 50 including an elongate body portion 21a having a longitudinal axis 22a and a circularly shaped side wall 23a spaced from axis 22a defining a chamber 25a for retaining fluid. Body portion 21a includes an open proximal end 31a, a distal end 32a and a passageway 33a therethrough in fluid communication with the chamber. A needle cannula 51 having a sharpened distal tip 52 and a lumen therethrough in fluid communication with passageway 33a projects outwardly from distal end 32a. Needle cannula 51 is attached to the distal end of the syringe barrel using adhesives or other suitable means. This embodiment of the present invention is especially suitable for use in an insulin syringe assembly for use by diabetics. These syringes frequently contain a permanently attached small diameter needle cannula preferred by diabetics because of medication regimens involving frequent injections. Side wall 23a includes a transparent portion having indicia 35a and contrast means 38a opposed from indicia 35a for improving readability of the indicia.

Figure 9:
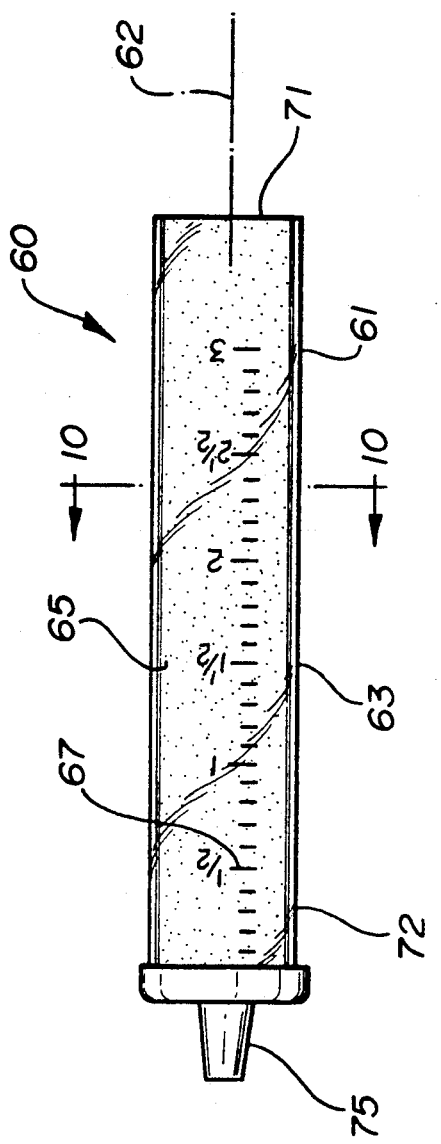
FIG. 9 is a side elevation view of another alternative embodiment of the syringe barrel of the present invention.
Figure 10:
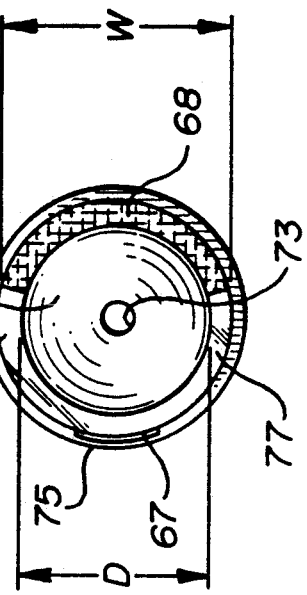
FIG. 10 is an enlarged cross-sectional view of the syringe barrel of FIG. 9 taken along lines 10—10.

Referring now to FIGS. 9 and 10, another alternative embodiment of the syringe barrel of the instant invention is illustrated. In this alternative embodiment a syringe barrel 60 having graphics visualization features comprises an elongate body portion 61 having a longitudinal axis 62 and a circularly shaped side wall 63 spaced from axis 62 defining an inside diameter D and a chamber 65 for retaining fluid. Body portion 61 includes an open proximal end 71 and a distal end 72 having a passageway 73 therethrough in fluid communication with chamber 65. Side wall 63 includes a transparent portion 77 having volume measuring indicia 67 running axially along side wall 63. Side wall 63 also includes contrast means in the form of contrast stripe 68 opposed from volume measuring indicia 67. The contrast stripe is axially oriented integral part of the side wall which makes that portion of the side wall less transparent than the transparent portion. As best illustrated in FIG. 10, contrast stripe 68 has a chordal width W which is equal or greater than the inside diameter D of the elongate body portion. In this embodiment, contrast stripe 68 is opaque.

Circularly shaped side wall 63, in this embodiment, may be formed by a co-extrusion process using thermoplastic resins which are substantially transparent to form transparent portion 77 and substantially opaque to form contrast stripe 68. Although less desirable, it is possible to make the transparent portion and the opaque portion separately and join the portions together using adhesive or other suitable means. It is also possible to form side wall 63 using two color molding so that the resin for the transparent portion and the resin for the contrast stripe are injected into the same mold cavity resulting in a unitary side wall suitable for use in the present invention. Clinical electronic thermometers made by two color molding and having a transparent window and an opaque body are taught in U.S. Pat. No. 4,743,121 to Takagi et al. When the circularly shaped side wall is formed in an extrusion process it will be necessary to provide additional components which are not made in the extrusion process such as frusto-conically shaped tip housing 75. This housing is attached to the side wall using adhesive, ultrasonic welding or other suitable means.

The syringe barrel of the present invention may be constructed of a wide variety of rigid materials with thermoplastic materials such as polypropylene, nucleated polypropylene, polyethylene and glass being preferred. Similarly, thermoplastic materials such as polypropylene, polyethylene and polystyrene are preferred for the plunger rod. A wide variety of materials such as natural rubber, synthetic rubber and thermoplastic elastomers are suitable for the stopper and the tip cap. A wide variety of commercially available inks may be used to form the indicia and/or contrast means on the syringe barrel. The inks and/or coatings usable for the instant invention should be of medical grade quality. It is desirable that the syringe barrel of the present invention be sterile when used. Accordingly, all components used in the syringe barrel should be chosen to withstand the sterilization process being utilized.

Thus, it can be seen that the present invention provides a simple, straight forward, reliable, easily fabricated, syringe barrel having means to improve the readability of the volume measuring indicia without the use of separate additional elements or devices. The present invention also provides for the improved readability of the volume measuring indicia when the syringe barrel is used near a background which is similar in color or shade to the volume measuring indicia.

What is claimed is:

1. A syringe barrel comprising:
   an elongate body portion having a longitudinal axis and a side wall spaced from said axis defining an inside diameter and a chamber for retaining fluid, said barrel portion having an open proximal end and a distal end having a passageway therethrough in fluid communication with said chamber;
   said side wall including a transparent portion having indicia; and
   said side wall including contrast means opposed from said indicia for improving readability of said indicia, said contrast means making said side wall within said contrast means less transparent than said transparent portion, said contrast means being of a substantially uniform color, said contrast means having a chordal width of equal or greater than said inside diameter.

2. The syringe barrel of claim 1 wherein said indicia comprises volume measuring indicia.

3. The syringe barrel of claim 1 wherein said indicia is black.

4. The syringe barrel of claim 1 wherein said contrast means is made of material being a color selected from the group of white, yellow, red, blue and combinations thereof.

5. The syringe barrel of claim 1 wherein said contrast means is opaque.

6. The syringe barrel of claim 1 wherein said contrast means is a coating on said side wall.

7. The syringe barrel of claim 6 wherein said contrast means is substantially axially oriented and elongately shaped.

8. The syringe barrel of claim 1 wherein said contrast means is integrally formed with said side wall and is a structural part of said side wall.

9. The syringe barrel of claim 8 wherein said side wall is formed by a co extrusion process.

10. The syringe barrel of claim 1 wherein said side wall is made of material selected from the group consisting of plastic and glass.

11. The syringe barrel of claim 1 wherein said indicia is printed on said side wall.

12. The syringe barrel of claim 11 wherein said side wall is made of thermoplastic material which is subject to a corona discharge treatment before said indicia is printed on said side wall.

13. The syringe barrel of claim 1 further including a needle cannula projecting outwardly from said distal end, said needle cannula having a sharpened distal tip and a lumen therethrough in fluid communication with said passageway.

14. The syringe barrel of claim 1 further including a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end; and
   a plunger rod having an elongate body portion engaging said stopper to facilitate operation of said stopper, said body portion extending outwardly from said proximal end of said barrel to form a syringe assembly.

15. The syringe assembly of claim 14 further including liquid medication in said chamber between said stopper and said distal end.

16. The syringe assembly of claim 15 further including sealing means for releasably sealing said passageway to retain said medication in said chamber.

17. A syringe barrel comprising an elongate body portion having a longitudinal axis and a circularly shaped side wall spaced from said axis defining an inside diameter and a chamber for retaining fluid, said body portion having an open proximal end and a distal end having a passageway therethrough in fluid communication with said chamber,
   said side wall including a transparent portion having volume measuring indicia running axially along said side wall; and
   said side wall including contrast means opposed from said volume measuring indicia for improving readability of said volume measuring indicia, said contrast means being of a substantially uniform opaque color, said contrast means having a chordal width of equal or greater than said inside diameter.

18. The syringe barrel of claim 17 wherein said contrast means is integrally formed with said side wall by a co-extrusion process.

19. The syringe barrel of claim 17 wherein said volume measuring indicia is printed on said side wall.

20. The syringe barrel of claim 17 wherein said side wall is made of thermoplastic material which is subject to a corona discharge treatment before said volume measuring indicia is printed on said side wall.

21. The syringe of claim 17 further including a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end;
   a plunger rod having an elongate body portion engaging said stopper to facilitate operation of said stopper, said body portion extending outwardly from said proximal end of said barrel to form a syringe assembly.

* * * * *